US010407471B2

(12) United States Patent
Cho et al.

(10) Patent No.: US 10,407,471 B2
(45) Date of Patent: Sep. 10, 2019

(54) COMPOSITION COMPRISING RECOMBINANT FUSION PROTEIN OF PATHOGENIC ANTIGEN PROTEIN AND FLAGELLIN OF VIBRIO VULNIFICUS FOR PREVENTING, ALLEVIATING, OR TREATING AGING

(71) Applicant: INDUSTRY FOUNDATION OF CHONNAM NATIONAL UNIVERSITY, Gwangju (KR)

(72) Inventors: Kyung A. Cho, Gwangju (KR); Jae Sung Lim, Gwangju (KR); Joon Haeng Rhee, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 15/801,467

(22) Filed: Nov. 2, 2017

(65) Prior Publication Data

US 2018/0118792 A1 May 3, 2018

Related U.S. Application Data

(62) Division of application No. 14/764,466, filed as application No. PCT/KR2013/002547 on Mar. 27, 2013, now abandoned.

(30) Foreign Application Priority Data

Nov. 30, 2012 (KR) ........................ 10-2012-0138234

(51) Int. Cl.
*C07K 14/315* (2006.01)
*A61K 38/16* (2006.01)
(Continued)

(52) U.S. Cl.
CPC ........ *C07K 14/3156* (2013.01); *A61K 38/164* (2013.01); *A61K 39/092* (2013.01);
(Continued)

(58) Field of Classification Search
CPC ...... A61K 39/395; A61K 39/00; A61K 39/02; A61K 39/12; A61K 39/21; A61K 39/35;
(Continued)

(56) References Cited

U.S. PATENT DOCUMENTS

2010/0291109 A1* 11/2010 Kedl .................. A61K 39/0008
424/173.1

FOREIGN PATENT DOCUMENTS

KR 2006-0118737 A 11/2006
KR 10-0795839 B1 1/2008
(Continued)

OTHER PUBLICATIONS

Nguyen et al., (Vaccine. Aug. 5, 2011;29(34):5731-9. Epub Jun. 13, 2011). (Year: 2011).*
(Continued)

*Primary Examiner* — Jana A Hines
(74) *Attorney, Agent, or Firm* — Clark & Elbing LLP; Susan M. Michaud

(57) ABSTRACT

The present invention relates to a composition for preventing, improving, or treating aging, wherein the composition comprises a recombinant protein of flagellin, which is the constituent of *Vibrio vulnificus* flagella, fused with a pathogenic protein antigen, as an active component. According to the present invention, the recombinant protein of the present invention can improve external and internal aging-related malfunctions and enhance immunity. Also, the composition of the present invention can easily perform immunization through mucosal administration.

Figure 1:
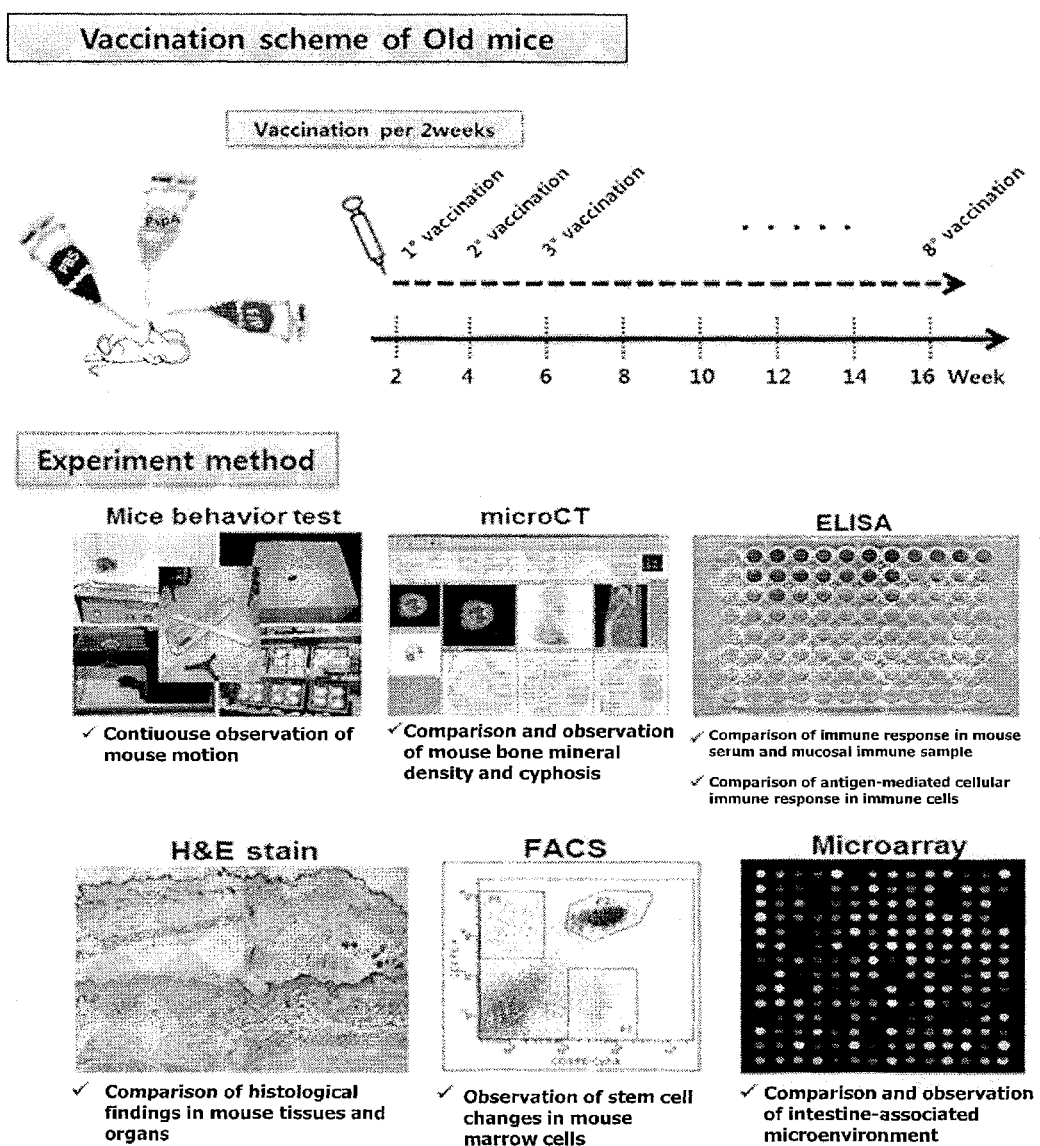

4 Claims, 8 Drawing Sheets

Specification includes a Sequence Listing.

(51) Int. Cl.
*A61K 39/09* (2006.01)
*A61K 39/02* (2006.01)
*C07K 14/28* (2006.01)
*A61K 39/00* (2006.01)

(52) U.S. Cl.
CPC ............ *A61K 39/107* (2013.01); *C07K 14/28* (2013.01); *A61K 2039/58* (2013.01); *C07K 2319/00* (2013.01)

(58) Field of Classification Search
CPC .......... A01K 67/00; A61P 29/00; A61P 31/04; A61P 31/10; A61P 31/12; A61P 31/18; A61P 33/00; A61P 35/00; A61P 37/04; A61P 37/08; C07H 21/04; C07K 14/435; C07K 16/28; C12N 1/19; C12N 1/21; C12N 5/10; C12N 15/63
USPC ......... 424/184.1, 204.1, 208.1, 234.1, 274.1, 424/275.1, 277.1; 435/252.3, 254.11, 435/320.1, 325, 348, 349, 366; 536/23.1, 536/23.5, 23.53, 23.7, 23.72, 23.74
See application file for complete search history.

(56) References Cited

FOREIGN PATENT DOCUMENTS

| KR | 20100114620 | * | 10/2010 | ........... A61K 39/106 |
| KR | 20100114620 A | * | 10/2010 | ........... A61K 39/106 |
| KR | 201001146200 A | | 10/2010 | |
| KR | 10-1130884 B1 | | 4/2012 | |
| WO | WO-2005/070455 A1 | | 8/2005 | |
| WO | WO-2007/098371 A2 | | 8/2007 | |

OTHER PUBLICATIONS

Komori et al., Eur J Pharmacol. Jul. 15, 2015;759:287-94. (Year: 2015).*
Roberston et al., (Kidney Int. Feb. 1983; 23(2):327-35) (Year: 1983).*
Scholz-Ahrens et al., (ISRN Rheumatology. vol. 2013, Article ID 460512, 12 pages) (Year: 2013).*
Baheti et al., "Cataract surgery in patients with history of uveitis," Saudi J Ophthalmol. 26(1):55-60 (2012).
International Search Report for International Application No. PCT/KR2013/002547, dated Jun. 14, 2013 (8 pages).
Kumar et al., "Topical flagellin protects the injured corneas from Pseudomonas aeruginosa infection," Microbes Infect. 12(12-13):978-89 (2010).
Lee et al., "A bacterial flagellin, Vibrio vulnificus FlaB, has a strong mucosal adjuvant activity to induce protective immunity," Infect Immun. 74(1):694-702 (2006).
Lotti et al., "Cataract as a complication of severe microbial keratitis," Eye (Lond). 6(Pt 4):400-3 (1992).
Nguyen et al., "Intranasal immunization with recombinant PspA fused with a flagellin enhances cross-protective immunity against *Streptococcus pneumoniae* infection in mice," Vaccine. 29(34):5731-9 (2011).

* cited by examiner

FIG. 6

| Mice No. | | Cellularity | Cell No. (/HPF) | | | Dysplastic feature | | | CD34 count/HPF |
|---|---|---|---|---|---|---|---|---|---|
| | | | Megakaryocytes | Myeloid | erythroid | Megakaryocytes | Myeloid | erythroid | |
| 1 | O-control (22 months) | 65% | 3 | preserved | preserved | (-) | (-) | (-) | 4~5 |
| 2 | O-control (25 months) | 95% | 4 | preserved | preserved | 1+ | (-) | (-) | 3~4 |
| 3 | O-PBS (1)(25 months) | 90% | 6 | preserved | preserved | (-) | (-) | (-) | 6~7 |
| 4 | O-PBS (2)(25 months) | 60% | 2 | preserved | preserved | 1+ | (-) | (-) | 6~7 |
| 5 | O-PspA(1)(25 months) | 90% | 2 | preserved | preserved | (-) | (-) | (-) | 7~8 |
| 6 | O-PspA(2)(24 months) | 80% | 5 | preserved | preserved | (-) | (-) | (-) | 3~4 |
| 7 | O-PspA(3)(24 months) | 95% | 6 | preserved | preserved | (-) | (-) | (-) | 8~9 |
| 8 | O-FP(1)(24 months) | 80% | 10 | preserved | preserved | 2+ | (-) | (-) | 10~12 |
| 9 | O-FP(2)(25 months) | 90% | 5 | preserved | preserved | (-) | (-) | (-) | 10~12 |
| 10 | O-FP(3)(25 months) | 80% | 6 | preserved | preserved | 1+ | (-) | (-) | 12~14 |

*FP; FlaB-PspA conjugated proteins*

Fig. 8
Spine
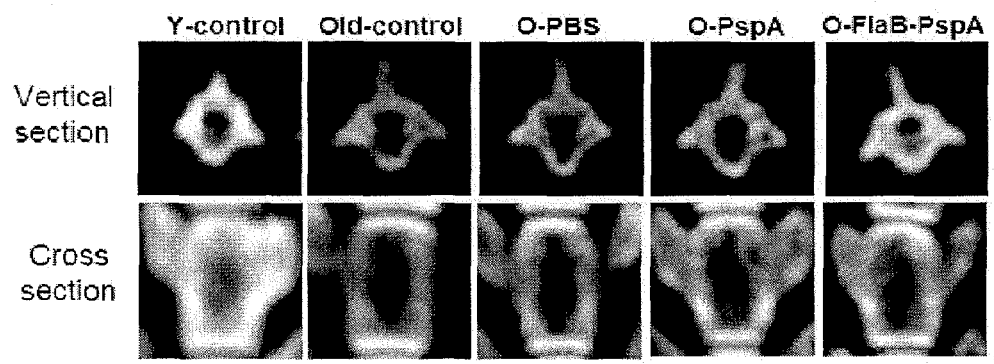
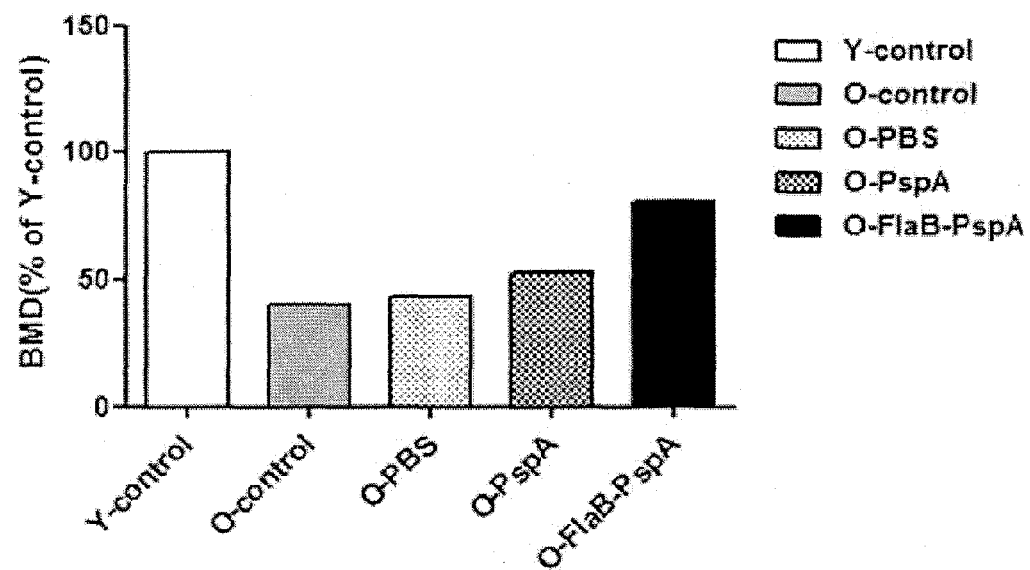

SEQUENCE LISTING

<160> NUMBER OF SEQ ID NOS: 1

<210> SEQ ID NO 1
<211> LENGTH: 612
<212> TYPE: PRT
<213> ORGANISM: Artificial Sequence
<220> FEATURE:
<223> OTHER INFORMATION: Synthetic Construct

<400> SEQUENCE: 1

```
Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
                20                  25                  30

Ser Ser Gly Phe Lys Ile Asn Ser Ala Lys Asp Asp Ala Ala Gly Leu
            35                  40                  45

Gln Ile Ser Asn Arg Leu Asn Val Gln Ser Arg Gly Leu Asp Val Ala
        50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Leu Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285

Glu Ser Val Ala Ile Val Asp Ala Ala Leu Lys Tyr Val Asp Ser His
290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350

Ile Leu Ser Gln Ala Ser Ser Ile Leu Ala Gln Ala Lys Gln Ala
        355                 360                 365

Pro Asn Ser Ala Leu Ser Leu Leu Gly Val Asp Ser Pro Val Ala Ser
370                 375                 380

Gln Ser Lys Ala Glu Lys Asp Tyr Asp Ala Ala Lys Lys Asp Ala Lys
385                 390                 395                 400

Asn Ala Lys Lys Ala Val Glu Asp Ala Gln Lys Ala Leu Asp Asp Ala
                405                 410                 415
```

-continued

```
Lys Ala Ala Gln Lys Lys Tyr Asp Glu Asp Gln Lys Lys Thr Glu Glu
            420             425             430

Lys Ala Ala Leu Glu Lys Ala Ala Ser Glu Glu Met Asp Lys Ala Val
            435             440             445

Ala Ala Val Gln Gln Ala Tyr Leu Ala Tyr Gln Gln Ala Thr Asp Lys
    450             455             460

Ala Ala Lys Asp Ala Ala Asp Lys Met Ile Asp Glu Ala Lys Lys Arg
465             470             475             480

Glu Glu Glu Ala Lys Thr Lys Phe Asn Thr Val Arg Ala Met Val Val
                485             490             495

Pro Glu Pro Glu Gln Leu Ala Glu Thr Lys Lys Lys Ser Glu Glu Ala
            500             505             510

Lys Gln Lys Ala Pro Glu Leu Thr Lys Lys Leu Glu Glu Ala Lys Ala
            515             520             525

Lys Leu Glu Glu Ala Glu Lys Lys Ala Thr Glu Ala Lys Gln Lys Val
    530             535             540

Asp Ala Glu Glu Val Ala Pro Gln Ala Lys Ile Ala Glu Leu Glu Asn
545             550             555             560

Gln Val His Arg Leu Glu Gln Glu Leu Lys Glu Ile Asp Glu Ser Glu
            565             570             575

Ser Glu Asp Tyr Ala Lys Glu Gly Phe Arg Ala Pro Leu Gln Ser Lys
            580             585             590

Leu Asp Ala Lys Lys Ala Lys Leu Ser Lys Leu Glu Glu Leu Ser Asp
            595             600             605

Lys Ile Asp Glu
    610
```

COMPOSITION COMPRISING RECOMBINANT FUSION PROTEIN OF PATHOGENIC ANTIGEN PROTEIN AND FLAGELLIN OF VIBRIO VULNIFICUS FOR PREVENTING, ALLEVIATING, OR TREATING AGING

TECHNICAL FIELD

The present invention was made with the support of the National Research Foundation of Korea, under Project No. 2012-0002472, which was conducted in the program titled "General Researcher Support Project/Female Scientist Support Project" in the project named "Research for the Mechanism of Aging Dependent Innate immune dysfunction" by the Chonnam National University under the management of the National Research Foundation of Korea, from May 1, 2010 to Apr. 30, 2013.

Furthermore, the present invention was made with the support of the Ministry of Knowledge Economy, Republic of Korea, under Project No. RTI-0501-01, which was conducted in the program titled "New Vaccines and Immune Disease Therapeutic Agents Development Project" in the project named "Development of Anti-aging Vaccine Adjuvant" by the Chonnam National University under the management of the Ministry of Knowledge Economy, Republic of Korea, from Jul. 1, 2011 to Jun. 30, 2012.

Furthermore, the present invention was made with the support of the Ministry of Education, Science, and Technology of Republic of Korea, under Project No. 2011-0030034, which was conducted in the program titled "Overseas Excellent Research Institutions Inducement Project" in the project named "Age-Related Cellular Function Regulation" by the Chonnam National University Hwasun Hospital under the management of the Ministry of Education, Science, and Technology of Republic of Korea, from Jul. 1, 2011 to Jun. 30, 2012.

This application claims priority from Korean Patent Application No. 10-2012-0138234 filed on Nov. 30, 2012, the disclosure of which is incorporated herein by reference.

The present invention relates to a composition for preventing, improving, or treating aging, the composition comprising a recombinant protein of flagellin, which is the constituent of *Vibrio vulnificus* flagella and an agonist of a toll-like receptor 5 (TLR-5), fused with a pathogenic antigen, and to a method for preventing, improving, or treating aging.

BACKGROUND ART

Humans are facing various problems not seen before due to the advent of an aging society caused by a prolonged average life span. In socio-economic aspects, the elderly sustenance allowance per head is expected to increase due to the increase in the elderly population and the reduction in the productive age population, and the interest in the improvement of the quality of life of the elderly is also a growing trend. As the social demands for the healthy and happy life of the elderly increase as described above, studies on the change in aging-related disease aspect and prevention of aging-related diseases are under active progress.

The aging process causes a wide variety of changes. Various changes appear, including reduced functions of respective main tissues, food intake and digestive disorders, reduced brain functions including defective memory, and reduced cardiovascular functions, as well as various appearance changes, such as skin wrinkles, hair decoloration, spine curving, and the change in motion. Moreover, these changes induce the reduction of functions and diseases of the respective tissues, and therefore, it is very important to understand causes of the reduction of external and internal functions due to aging and develop techniques of regulating the functions.

Besides, one of the large changes in functions due to aging is the reduction in immune function. This is called immunosenescence. When pathogens invade a host, the host defection action is made by two immune systems, an innate immune system and an adaptive immune system. Of these, the innate immune system is activated immediately after infection, to promptly regulate infecting pathogens, and takes charge of the initial infection until the adaptive immune system is activated. In this innate immune system, a receptor recognizing "pathogen associated molecular patterns (PAMPs) existing in the pathogens is called "pattern recognition receptors (PRRs), and these receptors are called toll-like receptors in a mammal. So far, 13 kinds of TLRs have been found, and studies on agonists of the respective TLRs have been actively conducted (Shizuo Akira et al, Cell, Pathogen Recognition and Innate Immunity, 124(4): 783-801, 2006). PRRs like TLRs exist on the cell surface or in the protoplasm, and have been known to regulate the innate immune response by various stimuli of PAMPs, and further regulate the adaptive immune response. Therefore, the agonists of TLRs may be target materials suitable for the development of various immunomodulators and vaccine adjuvants.

Of studies on aging, the fields that have received the most attention so far are the life span adjustment of aging or functional recovery of aging. Recently, studies on the extension of life span are rapidly increasing through various methods, such as by inhibiting the expression of a particular gene or overexpressing the particular gene in studies using drosophila models or nematodes, restricting diet, or treating with rapamycin. In addition, the interest in the maintenance of functions or recovery of functions, instead of the simple extension of life span, is also a growing trend. However, the regulation of a particular gene referring to the results shown in lower animal models may cause other functional side effects, and thus has a limitation in the application to humans. Moreover, the treatment with a drug, such as rapamycin, may greatly influence the immune function.

Throughout this application, various patents and publications are referenced, and citations are provided in parentheses. The disclosure of these patents and publications in their entities are hereby incorporated by references into this application in order to more fully describe this invention and the state of the art to which this invention pertains.

DETAILED DESCRIPTION OF THE INVENTION

Technical Problem

The present inventors have endeavored to develop a material capable of preventing, improving, or treating dysfunction due to aging. As a result, the present inventors have confirmed that the expressions of most toll-like receptors are reduced but toll-like receptor-5 is well expressed to keep functions thereof in aging immune cells, and confirmed that, when aged mice are immunized with a recombinant protein of flagellin, which is the constituent of *Vibrio vulnificus* flagella, fused with a pathogenic protein antigen of a pathogen, the immunity of the aged mice is activated and external and internal functions of the aged mice are improved, and thus have completed the present invention.

Therefore, an object of the present invention is to provide a composition for preventing, improving, or treating aging, the composition comprising, as an active ingredient, a recombinant protein of flagellin, which is the constituent of *Vibrio vulnificus* flagella, fused with a pathogenic protein antigen.

Another object of the present invention is to provide a composition for preventing, improving, or treating hair-related disease, the composition comprising the recombinant protein as an active ingredient.

Still another object of the present invention is to provide a composition for preventing, improving, or treating eye-related disease, the composition comprising the recombinant protein as an active ingredient.

Still another object of the present invention is to provide a composition for preventing, improving, or treating bowel disease, the composition comprising the recombinant protein as an active ingredient.

Still another object of the present invention is to provide a composition for preventing, improving, or treating bone disease, the composition comprising the recombinant protein as an active ingredient.

Another object of the present invention is to provide a method for preventing, improving, or treating aging.

Other objects and advantages of the present invention will become apparent from the detailed description to follow taken in conjugation with the appended claims and drawings.

Technical Solution

According to an aspect of the present invention, the present invention provides a composition for preventing, improving, or treating aging, the composition comprising, as an active ingredient, a recombinant protein of flagellin, which is the constituent of *Vibrio vulnificus* flagella, fused with a pathogenic protein antigen.

The present inventors have endeavored to develop a material capable of preventing, improving, or treating dysfunction due to aging. As a result, the present inventors have confirmed that the expressions of most toll-like receptors are reduced but toll-like receptor-5 is well expressed to keep functions thereof in aging immune cells, and confirmed that, when aged mice are immunized with a recombinant protein of flagellin, which is the constituent of *Vibrio vulnificus* flagella, fused with a pathogenic protein antigen, the immunity of the aged mice is activated and external and internal functions of the aged mice are improved.

The largest feature of the present invention is to use a recombinant protein of flagellin, which is the constituent of *Vibrio vulnificus* flagella, fused with a pathogenic protein antigen.

As used herein, the term "flagellin" refers to a unit molecule constituting flagella, which are the cilia to determine the mobility of bacteria. The flagellin of the present invention includes all flagellins that act as a TLR-5 activator of *Vibrio vulnificus*. According to an embodiment of the present invention, the flagellin of the present invention is FlaB, which is the flagellin of *Vibrio vulnificus*.

Examples of the pathogenic protein antigen usable herein may include an α-helix domain of surface protein A (PspA) and pneumococcal surface protein A (PsaA) of *Streptococcus pneumonia*; subunit hemagglutinin (HA) and neuraminidase (NA) of influenza virus; and spike (S) protein of severe acute respiratory syndrome virus (SARS virus), but are not limited thereto. According to an embodiment of the present invention, the pathogenic protein antigen is surface protein A (PspA) of *Streptococcus pneumonia*.

According to an embodiment of the present invention, the recombinant protein of the present invention is FlaB-PspA protein having an amino acid sequence of SEQ ID NO: 1.

As used herein, the term "aging" refers to a functional, structural, and biochemical procedure that continuously occurs in a subject from birth until death. The aging occurs in the overall cells and body tissues constituting the subject, and indicates the decrease in the metabolic rate, the increase in diseases, and the deterioration in adaptability, ultimately leading to death in cells and the whole body. For example, examples of aging include external changes, such as the increase in skin wrinkles, the reduction of hair gloss, hair decoloration, hair loss, the thickness reduction of the dermal layer in which hair follicles are present, the reduction in the number of follicles, spine curving, and the reduction in exercising; internal changes, such as the reduction in immune functions and the reduction in functions of main tissues; and the consequent occurrence of diseases of respective tissues, but are not limited thereto.

According to an embodiment of the present invention, the recombinant protein of the present invention enhances immunity. As used herein, the term "enhancing immunity" refers to keeping the immune response or activity of the in vivo immune system at a level of a non-aged control group or enhancing the same to a level of an aged control group. According to another embodiment of the present invention, the recombinant protein of the present invention prevents the reduction of functionality of immune-related organs due to aging or enhances the functionality compared with the aged control group, by increasing the production of secretory globulin A (secretory lgA, slgA) antibody, increasing the frequency of hematopoietic stem cells which are essentially associated with T cell differentiation, preventing thymic involution, or preventing the hypertrophy of mesenteric lymph nodes (MLNs) or spleens.

According to an embodiment of the present invention, the recombinant protein of the present invention prevents, improves, or treats the deteriorations in metabolic functions, functions of skin tissues, functions of intestinal tissues, functions of muscular tissues, brain functions, or cardiovascular functions. According to another embodiment of the present invention, the recombinant protein of the present invention prevents, improves, or treats the deteriorations in metabolic functions, functions of skin tissues, functions of intestinal tissues, or functions of muscular tissues. According to a particular embodiment of the present invention, the recombinant protein of the present invention prevents, improves, or treats the deteriorations in functions of the dermal tissue in which hair follicles are present, functions of large intestine tissues, or functions of muscular tissues.

According to another embodiment of the present invention, the present invention provides a composition for preventing, improving, or treating metabolic disease, the composition comprising the recombinant protein as an active ingredient.

As used herein, the term "metabolic disease" refers to a syndrome in which risk factors, such as obesity, diabetes, hypertriglyceridemia, hypertension, cardiovascular disease, and blood clotting, are shown together. The syndrome per se is not fatal, but has a predisposition to severe diseases, such as diabetes or ischemic cardiovascular diseases, resulting in a great threat to modern people. The syndrome was once called several names, including syndrome X, since the cause of the syndrome was not known, but recently, the syndrome was officially named metabolic syndrome or insulin resistance syndrome through adult treatment program III (ATP III) established by the World Health Organization and the US National Institutes of Health. According to an embodiment of the present invention, the metabolic disease of the present invention is obesity.

According to another embodiment of the present invention, the present invention provides a composition for preventing, improving, or treating hair-related disease, the composition comprising the recombinant protein as an active ingredient.

Examples of the hair-related disease which can be prevented, improved, or treated by the composition of the present invention include the reduction of hair gloss, hair decoloration, hair loss, the thickness reduction of the dermal layer in which hair follicles are present, the reduction in the number of follicles, and the like, but are not limited thereto.

According to still another embodiment of the present invention, the present invention provides a composition for preventing, improving, or treating bowel disease, the composition comprising the recombinant protein as an active ingredient.

Examples of the bowel disease which can be prevented, improved, or treated by the composition of the present invention include irritable bowel syndrome (IBS), uncontrolled diarrhea-associated irritable bowel syndrome (dIBS), Crohn's disease, traveler's diarrhea, ulcerative colitis, enteritis, small intestine bacterial overgrowth, chronic pancreatitis, pancreatic insufficiency, colitis, diverticular disease, hepatic encephalopathy, and hernia, but are not limited thereto. According to an embodiment of the present invention, the bowel disease of the present invention is enteritis or hernia. According to another embodiment of the present invention, the bowel disease of the present invention is colitis or hernia.

According to still another embodiment of the present invention, the present invention provides a composition for preventing, improving, or treating bone disease, the composition comprising the recombinant protein as an active ingredient.

Examples of the bone disease which can be prevented or treated by the composition of the present invention include osteoporosis, scoliosis, osteomalacia, rickets, bone metastasis of cancer cells, bone damage caused by bone metastases of cancer cells, osteolysis caused by bone metastases of cancer cells, fibrous dysplasia, aplastic bone disease, metabolic bone disease, rheumatoid arthritis, osteoarthritis, degenerative arthritis, and disc disease, but are not limited thereto. According to an embodiment of the present invention, the bone-related disease of the present invention is osteomalacia, metabolic bone disease, rheumatoid arthritis, osteoarthritis, or degenerative arthritis. According to another embodiment of the present invention, the bone disease of the present invention is osteoporosis or osteomalacia.

The composition for preventing, improving, or treating the foregoing diseases of the present invention contains the foregoing recombinant protein as an active ingredient, and thus descriptions of overlapping contents with the recombinant protein are omitted to avoid excessive complication of the specification due to repetitive descriptions thereof.

The composition of the present invention may be provided as a pharmaceutical composition.

According to an embodiment of the present invention, the composition of the present invention is a pharmaceutical composition comprising (a) a pharmaceutically effective amount of the recombinant protein any one of the recombinant proteins of the present invention; and (b) a pharmaceutically acceptable carrier. The term "pharmaceutically effective amount" refers to an amount enough to show and accomplish efficacies and activities of the recombinant protein of this invention as described above.

According to the present invention, the pharmaceutical composition may contain pharmaceutically acceptable carriers. The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition of this invention may be administered mucosally, orally, or parenterally, according to an embodiment, mucosally injection.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. Generally, suitable dosage unit for human host is to administer with the pharmaceutical composition in 0.001-100 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

The composition of the present invention may be provided as a food composition.

According to an embodiment of the present invention, the composition of the present invention is a food composition comprising (a) a sitologically effective amount of the recombinant protein any one of the recombinant proteins of the present invention; and (b) a sitologically acceptable carrier. When the composition of the present disclosure is prepared as a food composition, the food composition of the present disclosure may comprise, in addition to the recombinant protein of the present disclosure as active ingredients, ingredients commonly added for preparation of food. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.]) or a synthetic flavor (saccharin, aspartame, etc.). For example, when the food composition of the present disclosure is prepared as a drink, it may further comprise, in addition to the recombinant protein of the present disclosure as the active ingredient, citric acid, high-fructose corn syrup, sugar, glucose, acetic acid, malic acid, fruit juice, eucommia extract, jujube extract, licorice extract, or the like.

The composition of the present invention may be provided as a cosmetic composition.

In cases where the composition of the present invention is used to prepare a cosmetic composition, the composition of the present invention contains not only the foregoing recombinant protein but also ingredients normally used in the cosmetic composition, for example, a carrier and normally additives, such as an antioxidant, a stabilizer, a solubilizer, vitamins, a pigment, and a flavor.

As the carrier, purified water, monohydric alcohol (ethanol or isopropyl alcohol), polyhydric alcohol (glycerol, 1,3-butylene glycol or propylene glycol), higher fatty acid (palmitic acid or linolenic acid), oil (wheat germ oil, camellia oil, jojoba oil, olive oil, squalene, sunflower oil, macadamia peanut oil, avocado oil, soybean water-added lecithin or fatty acid glyceride) or the like may be used, but the carrier is not limited thereto. In addition, a surfactant, a sterilizer, an antioxidant, a UV absorber, an anti-inflammatory agent, and a refreshing agent may be added as needed.

The surfactant may include one selected from the group consisting of polyoxyethylene, hardened castor oil, polyoxyethylene, oleyl ether, polyoxyethylene monooleate, glyceryl monostearate, sorbitan monostearate, polyoxyethyelene monostearate, sorbitan, sucrose fatty acid ester, hexaglycerine monolaurate, polyoxyethylene reduced lanolin, POE, glyceryl pyroglutamate, isostearic acid, diester, N-acetylglutamine, and isostearyl ester.

The sterilizer may include one selected from the group consisting of hinoki thiol, triclosan, chlorhexidine gluconate, phenoxy ethanol, resorcin, isopropyl methyl phenol, azulene, salicylic acid, and zinc pyrithione.

As the antioxidant, any one of butyl hydroxyanisole, gallic acid, propyl gallate, and erythorbic acid may be used.

As the UV absorbent, any one of benzophenones such as dihydroxy benzophenone, melanin, para-amino benzoic acid ethyl, para-dimethylamino benzoic acid 2-ethylhexyl ester, cynocite, para-methoxy cinnamic acid 2-ethylhexylester, 2-(2-hydroxy-5-methylphenyl)benzotriazole, urocanic acid, and metal oxide microparticles may be used.

For the anti-inflammatory agent, glycyrrhetinic acid dipotassium or allantoin may be used, and as the refreshing agent, capsicum tincture or 1-menthol may be used.

The dosage form of the composition is any dosage form that can blend the recombinant protein as an active ingredient, and examples of the dosage form of cosmetics for preventing hair loss may include various forms of a sol, a gel, an emulsion, oil, wax, aerosol, and the like, such as hair tonic, hair cream, hair lotion, hair shampoo, hair rinse, hair conditioner, hair spray, hair aerosol, pomade, a powder, and a gel, but are not limited thereto.

In still another aspect of this invention, there is provided a method for preventing, improving, or treating aging, comprising administering to a subject in need thereof the composition of the present invention.

Advantageous Effects

The features and advantages of this invention will be summarized as follows:

(a) The present invention provides a composition for preventing, improving, or treating aging, the composition comprising, as an active ingredient, a recombinant protein of flagellin, which is the constituent of *Vibrio vulnificus* flagella, fused with a pathogenic protein antigen.

(b) The present invention provides a composition for preventing, improving, or treating metabolic disease, hair-related disease, eye disease, bowel disease, or bone disease, the composition comprising the recombinant protein as an active ingredient.

(c) The present invention can improve external and internal aging-related malfunctions and enhance immunity by using the recombinant protein of the present invention.

(d) The present invention can easily perform immunization through mucosal administration of the composition of the present invention.

BRIEF DESCRIPTION OF THE DRAWINGS

FIG. 1 shows a schematic view with respect to an experiment schedule and an experiment scheme for immunizing aged mice.

FIGs. 2A-2B show graphs illustrating measurement results of changes in food intake and body weight in aged mice according to the immuniziation with FlaB-PspA recombinant protein.

FIG. 3 shows morphological change results of aged mice through continuous immunization of an antigen.

FIG. 4 is an IgA reaction graph in aged mice by continuous immunization.

FIG. 5 illustrates histopathological findings with respect to the cutaneous histological change of aged mice by immunization with FlaB-PspA recombinant protein.

FIG. 6 shows the changes of hematopoietic stem cells in marrow cells of aged mice by immunization with FlaB-PspA recombinant protein.

FIG. 7 shows organs illustrating lymphatic system changes of aged mice by immunization with FlaB-PspA recombinant protein.

FIG. 8 shows the change in bone mineral density of aged mice by immunization with FlaB-PspA recombinant protein.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Materials and Methods

Aged mice (C57BL/6J, aged at least 23 months) were intranasally immunized with purified protein and recombinant protein continuously at two-week intervals. PspA protein and FlaB-PspA protein were purchased from the laboratory of professor Jun-haeng, Lee of the Clinical Vaccine Development Project Group of Chonnam National University.

All immunization experiments were conducted in the specific pathogen free (SPF) facility. Young mice (8-10 week old) were used for a control group. A non-immunized aged mouse group, an aged mouse group intranasally immunized with PBS (16 μl/mouse) 8 times or more at 2-week intervals, an aged group intranasally immunized with only PspA (2.5 μg/16 μl/mouse) protein 8 times or more at 2-week intervals, and an aged group intranasally immunized with FlaB-PspA (6.5 μg/16 μl/mouse) recombinant protein 8 times or more at 2-week intervals were used for immunization experimental groups.

The morphological and behavioral changes of the aged mice were observed during the continuous immunization.

Following the immunization, the body weight and feed intake of each mouse were measured every week. In order to accurately measure the changes according to the immunization, the mice were separately managed one by one. In addition, 50 g of feed was provided for each mouse, and then the remainder of the feed was accurately measured at one-week intervals. Also, the body weight of each mouse was accurately measured using an animal scale every week.

In order to compare morphological changes of aged mice according to the immunization, the appearances of the mice, that is, the hair condition, hair loss, and decoloration was observed and the anus or eyes were also continuously observed, thereby collecting changed patterns.

In order to compare the behavior changes of the aged mice according to the immunization, the behavioral changes of the mice were observed at a certain point during the immunization. In order to verify the behavioral ability of the mice, the aged mice of each group were placed in a confined space, and the motions of the mice were observed for a period of time. The motions were compared based on general standard items of mouse behavioral ability, that is, the motion, the number of times of standing on hind legs, the number of times of supporting using forelegs, and the number of times of touching the nose.

During the continuous immunization, in order to verify the change of the immune response depending on the number of times of immunization, blood and feces were collected from some mice, and then the change in antibody production was measured using enzyme-linked immunosorbent assay (ELISA).

After immunization for an appropriate period of time, several samples were collected from the overall mice, and then the entire changes of the aged mice according to the immunization were measured through various experiments.

In order to verify the change of the immune response according to the continuous immunization, serum and several mucous samples (feces, saliva, vaginal washing, etc.) were collected from the mice, and in order to compare the mucosal immune response, the change in secretory immunoglobulin A (secretory IgA, sIgA) production was measured by ELISA.

In order to compare the morphological changes of the aged mice according to the immunization, various tissues including the skin tissue were collected, and fixed with formalin prior to making a paraffin-block, and pathological findings were compared through Hematoxylin and Eosin (H&E) staining. In addition, with reference to the effect of immunization and the feed intake through the mucosal immune response, pathological findings of the tissues of small and large intestines, which largely account for the mucosal immunity, were compared and observed through H&E staining.

In order to compare the antigen-mediated cellular immune response with respect to lymphocytes separated from immune-related tissues, the lymphocytes were separated from the cervical lymph nodes and spleen and then the antigen-mediated cellular response was compared by ELISA. In addition, in order to compare and observe changed patterns of various bone marrow cells with respect to the cells separated from the bone marrow, the bone marrow cells were separated from hind legs of the aged mice, and the comparison was conducted using flow cytometry (FACS, Beckman Coulter). Particularly, the frequency of hematopoietic stem cells essentially associated with T cell differentiation was compared and observed through immuno-staining using CD34, which is a hematopoietic stem cell indicator.

In order to compare the change in bone mineral density (BMD) of the aged mice according to the immunization with respect to spines separated from the mice, the spines were extracted from the mice, and then the bone mineral density (BMD) according to the continuous immunization and kyphosis according to aging of the aged mice were compared and observed using micro-computer tomography (microCT: Skyscan 1172, Micro Photonics Inc., US).

Next, for the ongoing study, the morphological and behavioral changes of the aged mice according to the continuous immunization were compared and compared in connection with metabolism. For this, after the blood was collected from the aged mice, the serum or plasma was separated therefrom, and then the changes in hormone-related and metabolism-related genes were compared. In addition, in order to compare and observe the change in mucosal immunity according to the immunization, the intestine-associated microenvironment was compared using normal microbiota. In addition, the blood and feces were collected from the aged mice continuously immunized with antigens, and then the gene expression pattern was compared and observed through advanced analysis methods, such as microarray.

Results

Example 1

Changes in Feed Intake and Body Weight in Aged Mice Immunized with Flagellin-PspA Recombinant Protein While the aged mice were intranasally immunized eight times at two-week intervals, the body weight and the feed intake of the mice of each group were measured. The non-immunized aged mice were used as a control group.

The aged mice were intranasally immunized eight times with phosphate buffered saline (PBS), prepared 2.5 μg of PspA, and 6.5 μg of FlaB-PspA recombinant protein at two-week intervals. The body weight and the feed intake of the mice of each group were measured every week. The measurement results are shown in FIGS. 2a and 2b.

Figure 2A:
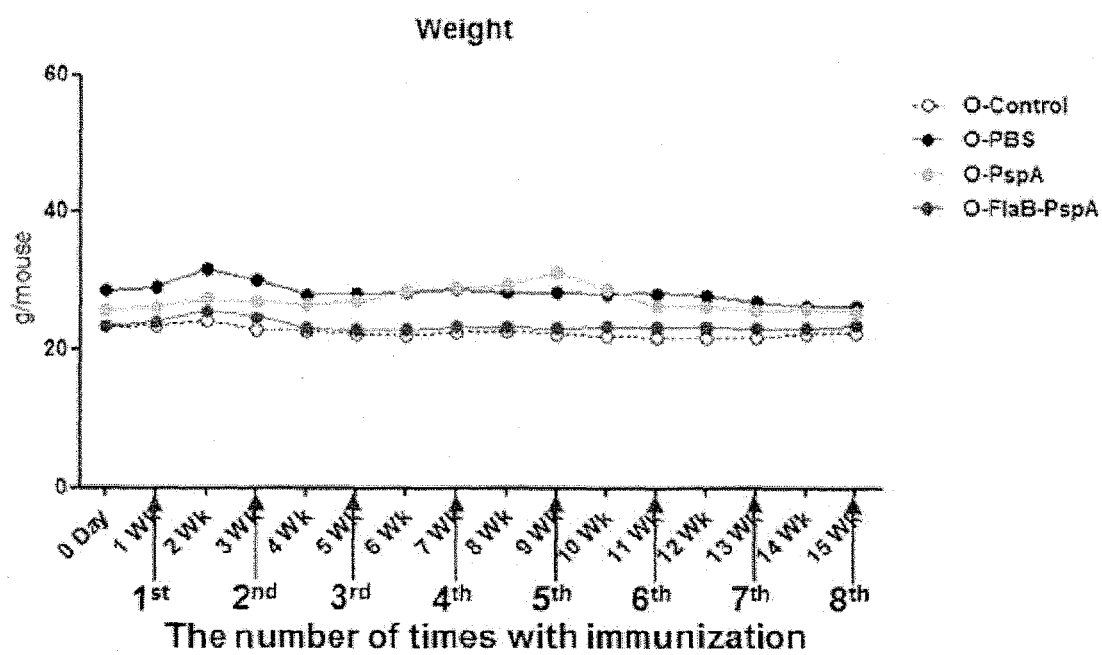
Figure 2B:
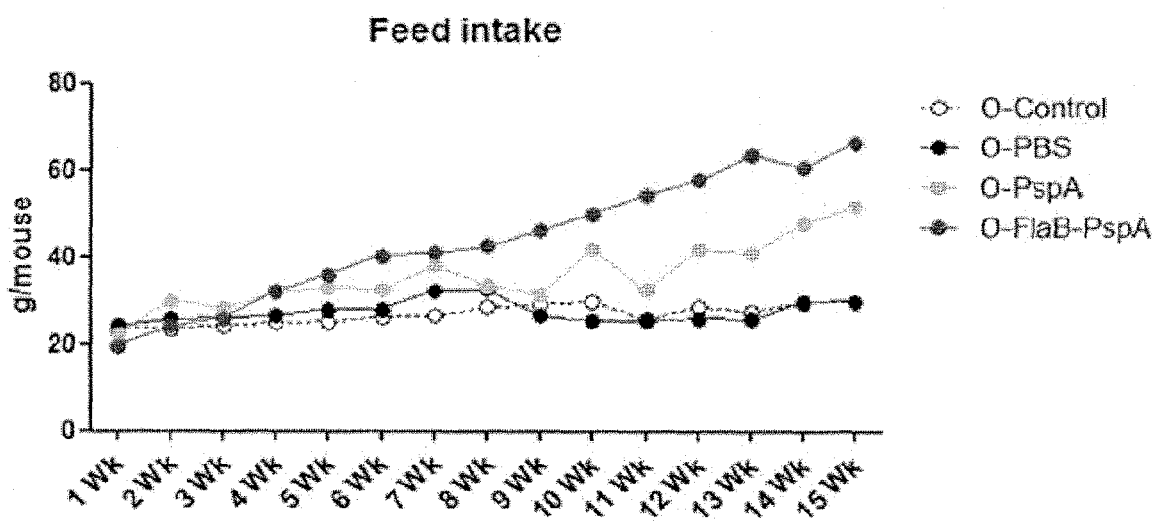

As a result of body weight measurement, it was verified that the non-immunized mouse group, the group immunized with PBS, the group immunized with PspA alone, and the group immunized with FlaB-PspA recombinant protein showed no change in body weight due to the immunization (FIG. 2a).

As a result of comparing the feed intake of the aged mice according to the immunization, the non-immunized mouse group showed no great change in the feed intake over time, and the group immunized with PBS also showed no great change in the feed intake, regardless of eight times of immunization at two-week intervals. On the other hand, the group immunized with PspA alone was verified to show a gradual increase in the feed intake during the continuous immunization. Particularly, it was shown that the group immunized with FlaB-PspA recombinant protein showed an increase in the feed intake through the continuous immunization, and here, the rate in increase of the feed intake was significantly higher than that of the group immunized with PspA alone (FIG. 2b).

As can be seen from the results of example 1, it can be confirmed that, when the aged mice are continuously immunized with antigens, the body change is not greatly changed, but the feed intake is greatly increased. Particularly, it can be seen that the immunization with a recombinant protein including a vaccine adjuvant fused with a pathogenic antigen significantly increases the feed intake.

Example 2

Figure 3:
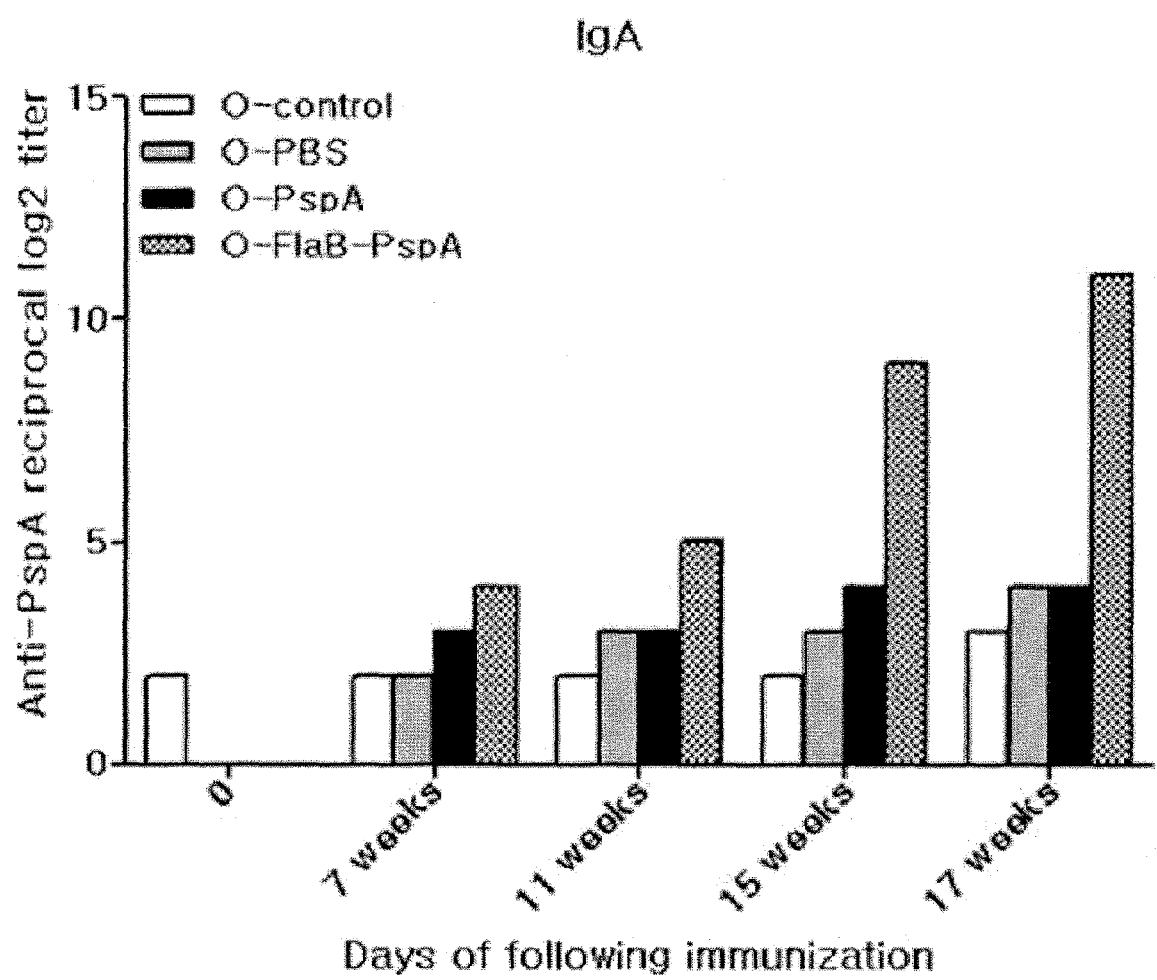

Observation of Morphological Changes of Mice Through Continuous Immunization with Antigen While the aged mice were intranasally immunized eight times at two-week intervals, the morphological changes of the mice according to the immunization were monitored every week. The results are shown in FIG. 3. The non-immunized aged mice were used as a control group.

The aged mice prior to the immunization had no abnormal findings by appearances. There were no abnormal findings in view of hair condition, hair luster, hair decoloration, hair loss, the anus (colitis or hernia), or the eyes (cataracts).

However, as a result of observing the aged mice following the immunization, it was verified that the non-immunized aged mouse group had a worse hair condition than the group immunized eight times at two-week intervals, and the appearances became generally worse, such as a severe progression of hair decoloration or hair loss. Besides, normal findings, such as hernia, were severely shown in the anus, and abnormal findings, such as suspected cataracts, were severely shown also in both eyes (O-control). The group immunized with PBS also had a bad hair condition, and the appearances thereof became severely worse, such as severe progressions of hair decoloration and hair loss. In addition, findings of slight colitis or hernia were shown in the anus, and findings of suspected cataracts were severely shown in one eye (O-PBS).

On the other hand, as a result of eight times of immunization with PspA, slight decoloration was shown but the hair loss was not severe in the appearance of the aged mice, and abnormal findings were not observed in the anus or eyes (O-PspA). Particularly, it was verified that, the group immunized with FlaB-PspA recombinant protein had a good hair condition so that the hair condition of the aged mice of the group was very similar to that of the aged mice prior to the immunization, and abnormal findings were observed in neither the anus nor eyes (O-FlaB-PspA).

As can be seen from the results of example 2, it can be verified that the appearances of the aged mice are better through the continuous immunization. It is general that the aging causes a severe progression of hair decoloration or hair loss and abnormal findings, such as cataracts occurring in eyes. Rodents showed abnormal findings, such as hernia, in the anus due to the reduction in the muscle amount. However, the continuous immunization with antigens could be verified to prevent the occurrence of such abnormal findings. Particularly, it can be seen that, as for the group immunized with a recombinant protein including a vaccine adjuvant fused with a pathogenic antigen, the appearances of the aged mice are maintained over time or have a better condition.

Example 3

Figure 4:
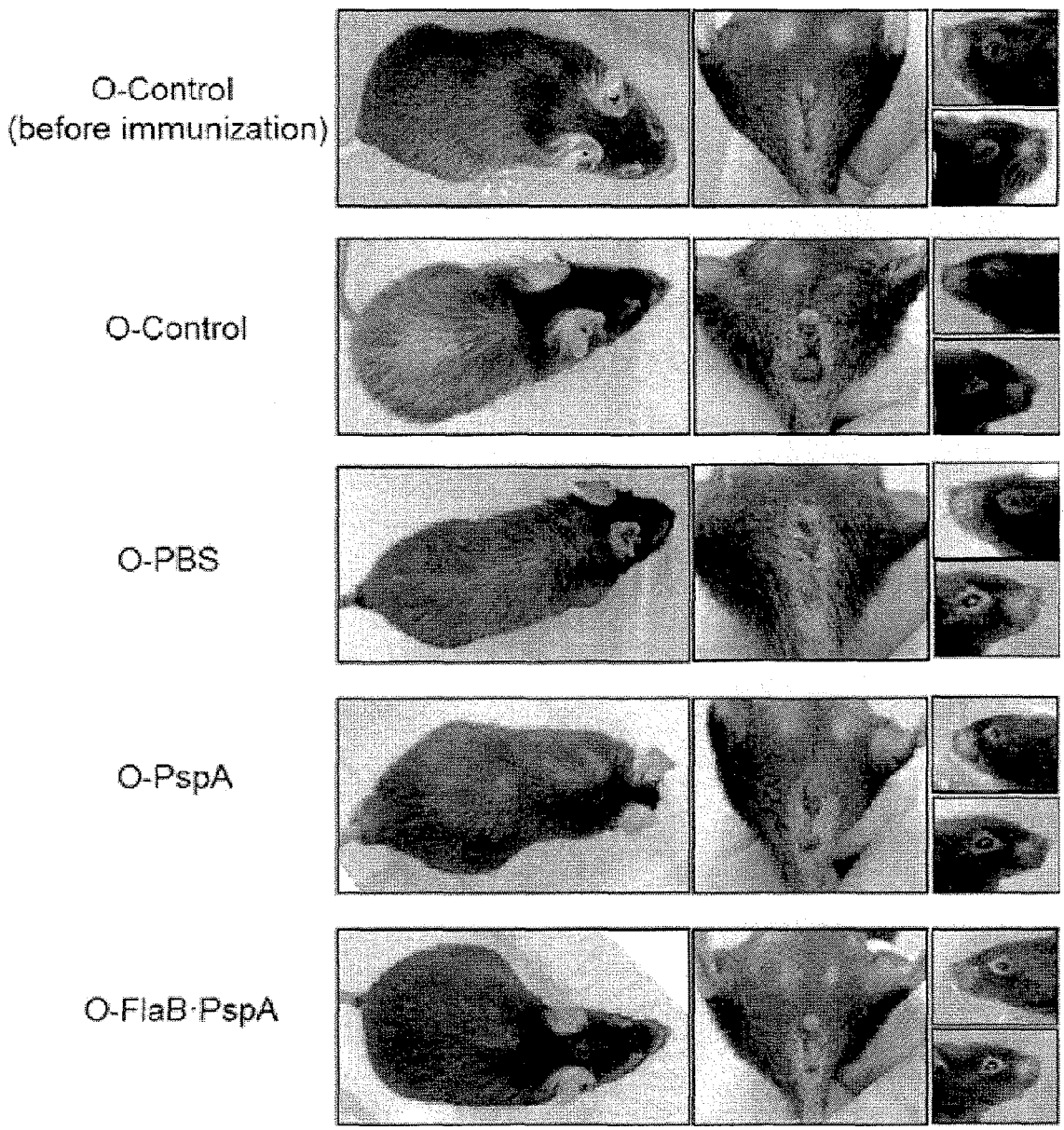

Change in IgA Reaction of Aged Mice Through Continuous Immunization with Antigen During the continuous immunization, the feces were collected from the mice of each group after each immunization to verify the IgA reaction of the aged mice according to the immunization by ELISA. The results are shown in FIG. 4. The non-immunized aged mice were used as a control group.

The non-immunized aged mice had no great difference in the IgA response during the immunization (O-control). It was verified that the group immunized with PBS alone showed no great difference in the IgA response, and then showed a slight increase in the IgA response after the sixth immunization, but there is no great increase in the IgA response (O-PBS). The group treated with PspA alone showed the IgA response after the fourth immunization, but showed no great difference after that (O-PspA). Whereas, as for the group immunized with FlaB-PspA recombinant protein, the IgA response was significantly increased depending on the number of times of immunization (O-FlaB-PspA).

As can be seen from the results of example 3, it was verified that, as a result of verifying the IgA reaction with respect to the mucosal immune reaction of the aged mice through the continuous immunization, the IgA reaction was significantly increased depending on the immunization in the group immunized with FlaB-PspA recombinant protein while no great change in the IgA reaction or a slight IgA reaction was shown in the other groups. Judging from the results, the mucosal immunity of the aged mice is activated by the recombinant protein.

Example 4

Figure 5:
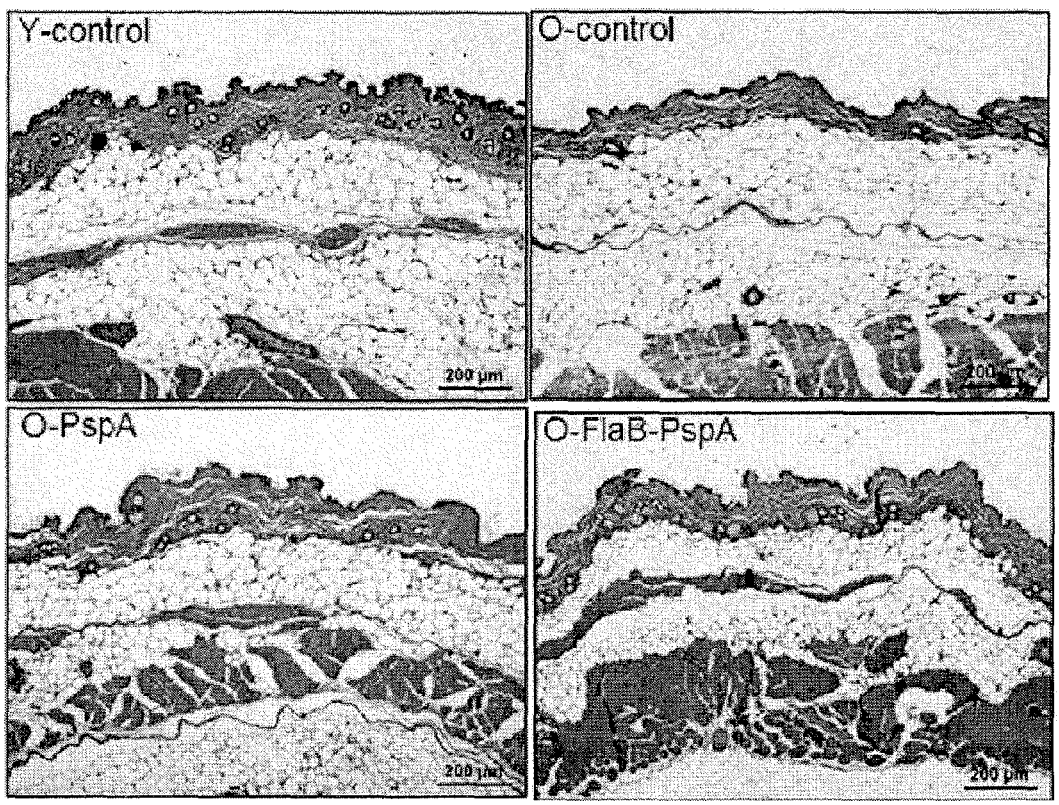

Skin Histological Change of Aged Mice Through Immunization with Recombinant Protein The results of example 2 indicated that the hair condition of the aged mice became very favorable in the group continuously immunized with antigens, particularly, the recombinant protein. In order to prove these results in more detail, the results were confirmed through H&E staining. The H&E staining results are shown in FIG. 5. Young mice were used as a control group.

As a result of verifying H&E staining on the skin tissue of the back of the aged mice, it is general that the aging causes the progression of hair loss and the thinning of the dermis layer. It can be confirmed that, as for the young mice, the dermis layer is thick and a lot of hair follicles, that is, where hairs grow, exist in the dermis layer (Y-control). Whereas, it can be confirmed that, as for the aged mice, the dermis layer become thin and the number of hair follicles is significantly reduced (O-control). It could be verified that, when the aged mice were continuously immunized with an antigen (O-PspA) and a recombinant protein (O-FlaB-PspA), the dermis layer became thickened and the number of hair follicles was increased. Particularly, it could be verified that the number of hair follicles was significantly increased in the group immunized with FlaB-PspA recombinant protein.

As can be seen from the results of example 4, the histological assay confirmed that the continuous immunization with antigens improved the morphological findings of the aged mice (results of example 2). It could be confirmed through the histological assay that the amelioration of the progression of hair decoloration and hair loss of the aged mice, shown in the results of example 2, is due to the fact that the hair follicles are maintained in the aged mice due to the continuous immunization. In view of the results, it can be seen that the continuous immunization with the recombinant protein slows or prevents the progression of hair decoloration and hair loss occurring due to aging.

Example 5

Change in Bone Marrow Cells in Bone Marrow Through Immunization with Recombinant Protein The change in bone marrow cells in the bone marrow of the aged mice through the continuous immunization was verified, and the results are shown in FIG. 6. Non-immunized aged mice were used as a control group.

As a result of observing the change in bone marrow cells with respect to cells separated from the bone marrow of the aged mice, there is no difference between groups in view of cellularity.

As a result of confirming the proportions of bone marrow cells (megakaryocyte, myeloid, and erythroid lineages), it was verified that the bone marrow cells were generally well maintained and differentiated in the aged mice.

In addition, as a result of verifying the frequency of hematopoietic stem cells through immuno-staining using CD34, which is a hematopoietic stem cell indicator, it could be verified that CD34 was increased in the aged mice continuously immunized with FlaB-PspA recombinant protein rather than in the other groups.

As can be seen from the results of example 5, it could be verified that the continuous immunization with the recombinant protein is associated with not only the changes in the simple appearances but also the immune-related effects in the old mice.

Example 6

Figure 7:
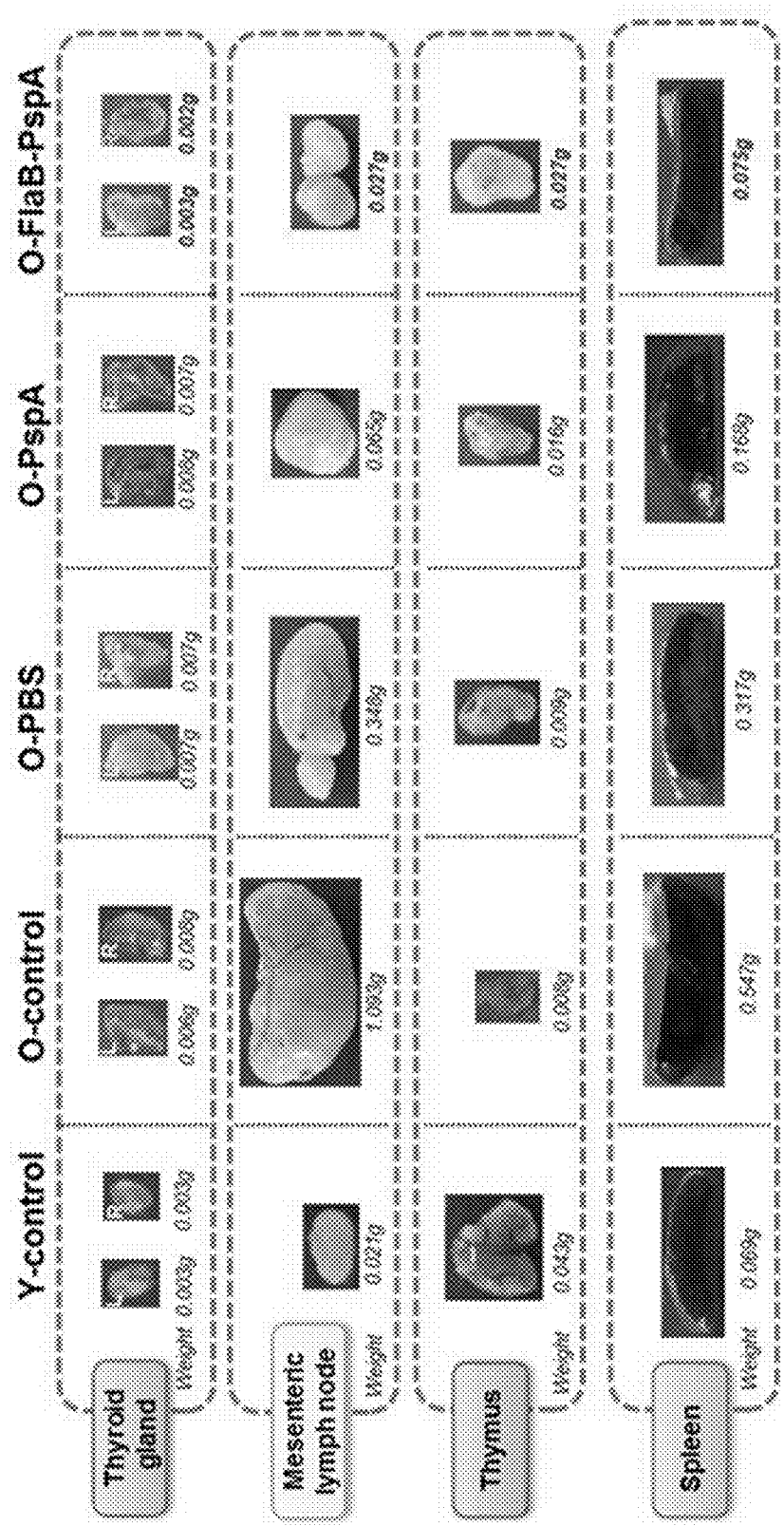

Changes of Lymphatic System Organs Through Immunization with Recombinant Protein After the continuous immunization for an appropriate period of time, organs were extracted from the mice of each group, and the morphology and weight of each organ were measured. The measurement results are shown in FIG. 7. Young mice were used as a control group.

The tissues were extracted from the aged mice, and the morphological change and weight of each of the organs were measured. As a result, the difference caused by the continuous immunization was observed in the lymphatic system-related organs rather than in the other organs. Particularly, it was verified that the morphology and weight of the organs in the group immunized with FlaB-PspA recombinant protein were similar to those of the young mice.

Thymic involution with age is a general phenomenon, but it was verified that the thymus weight was increased in the aged mouse groups continuously immunized with antigens, and particularly, the thymus weight was significantly increased in the group immunized with FlaB-PspA recombinant protein. Besides, even though the mesenteric lymph nodes (MLNs) or the spleen, which are frequently used for systemic inflammation responses, mostly undergo a very hypertrophic morphology with age due to the continuous infection, it was verified that the thymus weight was larger in the aged mice continuously immunized with FlaB-PspA recombinant protein rather than in the other groups; and the spleen weight was smaller in the aged mice continuously immunized with FlaB-PspA recombinant protein rather than in the other groups, and the spleen morphology of the aged mice continuously immunized with FlaB-PspA recombinant protein was also similar to that of the young mice.

As can be seen from the results of example 6, it could be verified that the aged mice continuously immunized with antigens exhibited improved morphological features of the immune-related organs. Particularly, the aged mice immunized with FlaB-PspA recombinant protein were observed to have very similar organ morphological findings to the young mice.

Example 7

Change in Bone Mineral Density of Aged Mice Through Immunization with Recombinant Protein Spines were extracted from the aged mice, and the change in bone mineral density through the immunization with the recombinant protein of the aged mice was measured using micro-computer tomography (microCT). The measurement results are shown in FIG. 8. Young mice were used as a control group.

After eight times of continuous immunization, the spines were extracted from the aged mice, and the change in bone mineral density through immunization was measured using microCT. As a result, it could be verified that the bone mineral density was significantly improved in the group immunized with the recombinant protein. In connection with example 1, it could be thought that the facts that the body weight was not changed depending on the number of times of immunization and the feed intake was increased in only the group immunized with the recombinant protein are associated with the motion quantity of the aged mice, and it could be explained that, in this regard, the bone mineral density was more significantly increased in the group continuously immunized with the recombinant protein rather than in the other aged mouse groups.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for improving or treating age-related osteoporosis, the method comprising administering to a subject an effective amount of a composition comprising a recombinant protein of flagellin, which is a constituent of *Vibrio vulnificus* flagella, fused with a protein antigen of a pathogen, as an active ingredient,
wherein the protein antigen of a pathogen is surface protein A (PspA) of *Streptococcus pneumonia*.

2. The method according to claim 1, wherein the flagellin is FlaB, which is flagellin of *Vibrio vulnificus*.

3. The method according to claim 1, wherein the recombinant protein is FlaB-PspA protein comprising the amino acid sequence of SEQ ID NO: 1.

4. The method according to claim 1, wherein the recombinant protein enhances immunity.

* * * * *